United States Patent [19]

Johnson, Jr.

[11] Plant 4,768

[45] Sep. 22, 1981

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 153,393

[22] Filed: May 27, 1980

[51] Int. Cl. ..... A01H 5/03

[52] U.S. Cl. ..... Plt./48

[58] Field of Search ..... Plt./48

*Primary Examiner*—Robert E. Bagwill

*Attorney, Agent, or Firm*—Townsend & Townsend

[57] ABSTRACT

A new distinct spring bearing variety of strawberry plant characterized by its prolific runner production and ability to produce large, glossy, smooth berries throughout the first and second fruiting seasons. The variety is particularly distinguished by having one leaf per plant generally with four or five leaflets rather than three, and further by an abundance of pubescence with pedicel hairs which grow substantially perpendicular to the pedicel. The large fruit and strong pedicel will make the variety popular for "long stem" use.

2 Drawing Figures

This invention relates to a new and distinct variety of strawberry plant which is the result of a cross of the Driscoll patented spring variety U.S. Plant Pat. No. 3,286 and Driscoll everbearing selection E12.

The seedlings resulting from the aforementioned cross were grown and asexually multiplied in Shasta County, Calif. and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced by runners in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Figure 1:
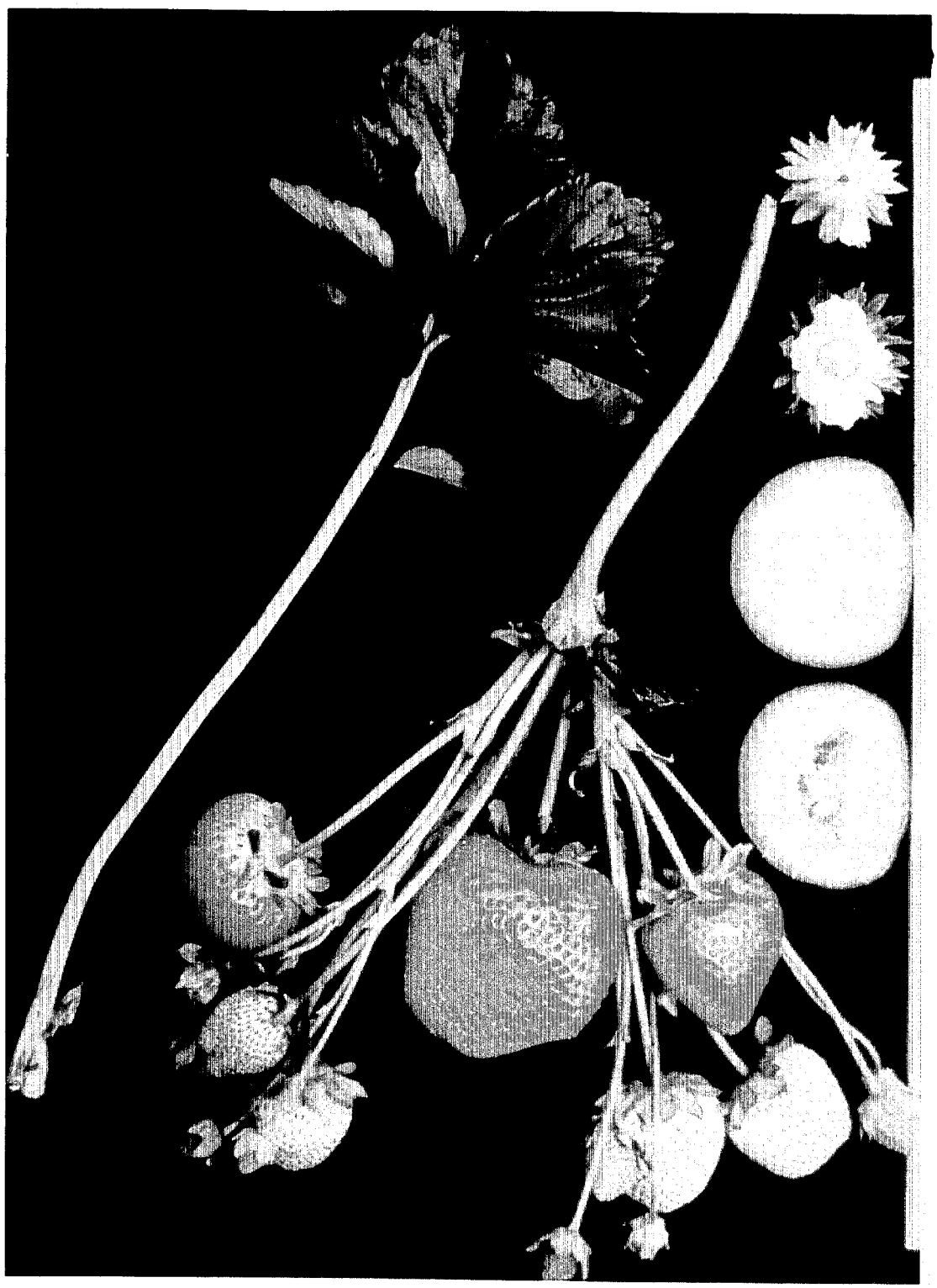
FIG. 1 illustrates plant parts of the new variety which are typical in size, shape and color during July.
Figure 2:
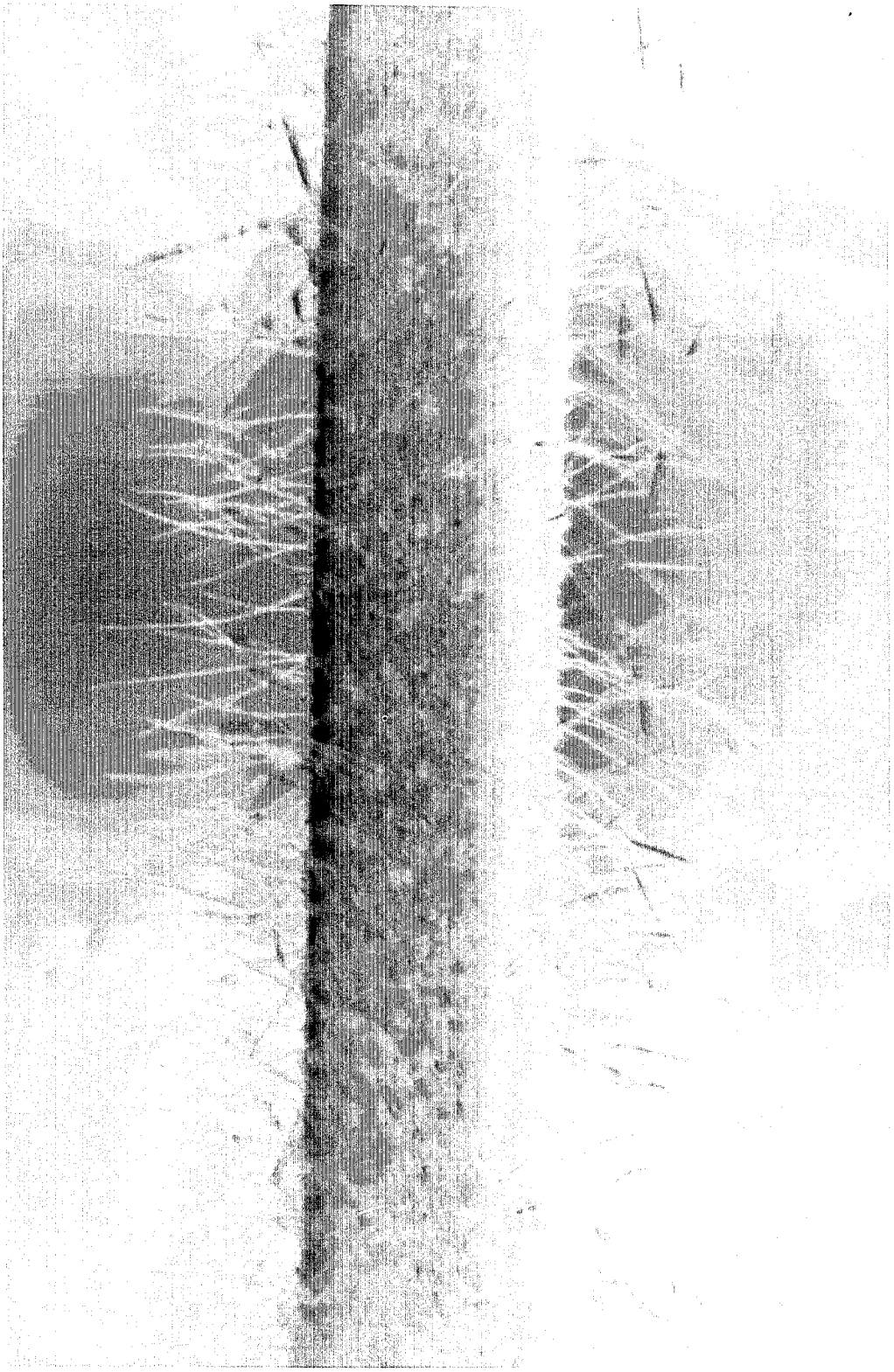
FIG. 2 illustrates the distinctive orientation of pedicel hair growing perpendicular to the pedicel.

Referring more particularly to FIG. 1, there is shown the strong, heavy common or main peduncle and the axil with the pedicel holding the primary berry originating from that axil. Also illustrated are four secondary peduncles also originating from the axil and at least ten berries which will be large enough to be shipped to the fresh market from this inflorescence. The primary as well as secondary and tertiary berries of the new variety are large. The primary berry illustrated is over 50 mm. in length and width. The leaf illustrated is the strongest distinguishing characteristic of the new variety as there are four leaflets per leaf. There is generally one leaf per plant with either four or five leaflets, in contrast to the normal three, whether the plant is growing at the nursery or the fruiting bed.

The plant of this novel spring fruiting variety is medium to large in size, but usually lower to the ground than the patented spring bearing variety Heidi, U.S. Plant Pat. No. 3,123. The plant is darker than Heidi even though the young leaves may be lighter in color until they mature. Even though a spring bearing variety, if given the correct chilling before planting, this variety will produce during the first year after being planted similarly to Heidi.

The crown crop ripens generally in April with the main crop ripening during mid or late May, slightly before Heidi. It will not, however, produce as heavily during late summer and fall and will not produce the first year continuously if given the chilling the Heidi is able to receive and still produce. The fruit is consistently larger and has a heavier, thicker pedicel than Heidi. The inflorescence of the new variety tends to produce more secondary peduncles, thus more berries per inflorescence than Heidi. The fruit becomes darker, generally less conic and even though it is not prone to consistent longitudinal furrows and is considered smooth, it is not as smooth as Heidi. The flesh and skin are not as firm as Heidi. The flavor when compared during a taste panel is equal to Heidi and the strawberry aroma is also equal to Heidi. The large fruit and strong pedicel make the variety popular for supplying the need for "long stems" (when the fruit is sold with several inches of the pedicel accompanying the fruit).

The new variety is distinct because of its pubescence. It is not so abundant to be objectionable, but is more abundant on all plant parts than Heidi. The hair on the pedicel is perpendicular to the pedicel in contrast to Heidi where the hair is parallel to the pedicel. The inflorescence may be as conspicuous above the plant as Heidi, but later in the fruiting season the number of inflorescence per plant is less. The inflorescence is longer in total length than Heidi to the point that it is a detriment as fruit may reach down in the irrigation furrow.

The new variety is more prone to be susceptible to powdery mildew than Heidi, but is equal to Heidi in its susceptibility to the other California pests, two-spotted mite, thrip, lygus and cyclamen mite. It appears to be more susceptible to bacterial leaf spot *Xanthomonas fragariae* and the common leaf spot *Mycosphaerella fragariae*. It has not been completely tested against the Verticillium or the Red Stele diseases. Runners are abundant at the nursery and more abundant in the fruiting bed if given the same winter chilling as Heidi. As a seedling and selection, this variety withstood the natural invasions of certain virus components found in Central California without losing its ability to produce.

The varietal characteristics of the novel plant, described below in detail, were observed mainly during the first season, but second year fruit will be referred to. Observations were made during July and August in the Watsonville area of California which is a cool coastal area near the Pacific Ocean. The color terminology is in accordance with the Munsell Color System.

Plant: Medium to large, vigorous, especially if given adequate chilling before being planted, and has an extensive root system. Isozymes in Leaf Extracts. Phosphoglucoisomerase (PGI): Five banded pattern usually called "Auk Lake" or A7 pattern. It is a dihybrid type with bands at 25/30/35 mm. under the standardized test done by University of California (Scandolios. 1969 Biochem. Genet. 3:37–79).

Leaves: Medium to large in size. The central leaflet is usually 6 to 9 cm. in width with the length slightly greater than the width. One leaf per plant generally has four or five leaflets rather than three. Petiole length is mostly 15 to 20 cm. from the base to the petiolule. Bracts may be present on the petiole. Leaflets are mostly cupped upward. The leaflets are moderately to strongly rugose. The leaflet serrations are deep and acute at the apex. The color of the upper side of the leaflet during July is 0.6-G.2.8/6.5.

Runners: Runners are vigorous and abundant at the nursery. If the plant, however, is given a mean temperature of less than 50° F. after planting in the fruiting beds for the months of December, January and February and dug from high elevation by Nov. 1 and given two weeks storage at 34° F., less than one runner per plant can be expected.

Inflorescence: Total length varies from 25 to 35 cm. becoming longer as the season progresses. The peduncles and pedicels are thick and considered strong. The pedicel holding the primary berry originates mainly at an axil where as many as four or five secondary peduncles may also originate. Ten or more berries may originate from an inflorescence when there are many secondary peduncles present. The primary berry ripens closer to the axil than secondary or tertiary berries. There may be, however, simpler inflorescences with as few as one secondary peduncle, but the secondary berries are generally still farther away from the common peduncle than the primary berry. The hair on the pedicel 20 mm. from a tertiary berry is perpendicular to the pedicel. Flowers are large and showy and may be visible above the plant during the spring and early summer. Anthers produce an abundance of pollen.

Fruit: Crown crop berries are medium in size, but large for crown crop fruit. Main crop and subsequent berries consistently large. Primaries 45 mm. to 55 mm. in length and width. Secondary and tertiary berries large even though smaller than primaries. Holds large size both first and second year until end of fruiting season with only slight drop in size. Flesh and skin considered moderately firm. Fruit shape is mainly short wedge to conic in outline with rounded shoulders at the calyx end and not necked (USDA Bulletin 1043). Some longitudinal furrows on primaries, but mainly a smooth surface. Not prone to malformation. Usually has glossy, good appearance. The tips are not normally green or seedy, but shoulders may be slow to ripen, especially in the spring. Surface is considered dark—5.5R-2.9/11.6—flesh is 8.4R-4.0/15.6. The seed is mostly exerted small to medium in size. Yellow in color, but darken rapidly if exposed to direct sunlight.

Calyx: Considerable variation in size and shape. Summer calyx may be small in comparison to fruit size. 30 mm. or less in diameter and individual sepals elliptical to slightly ovate with small serrations and overlapping. The calyx of some primaries large, over 40 mm. in diameter with individual sepals strongly ovate to wide elliptical with strong serrations and overlapping. Color of sepals on side facing fruit 8.7GY-5.7/12.3.

I claim:

1. The new and distinct strawberry plant herein described and illustrated, and identified by the characteristics enumerated above.

* * * * *